United States Patent [19]

Sanders et al.

[11] Patent Number: 5,130,457

[45] Date of Patent: Jul. 14, 1992

[54] PROCESS FOR THE PREPARATION OF N,N-DISUBSTITUTED MONO- AND OLIGOURETHANES

[75] Inventors: Josef Sanders, Cologne; Dieter Dieterich, Leverkusen, both of Fed. Rep. of Germany

[73] Assignee: Bayer Aktiengesellschaft, Leverkusen, Fed. Rep. of Germany

[21] Appl. No.: 25,910

[22] Filed: Mar. 16, 1987

[30] Foreign Application Priority Data

Mar. 22, 1986 [DE] Fed. Rep. of Germany ....... 3609813

[51] Int. Cl.$^5$ ............... C07C 271/12; C07C 271/24; C07C 271/34; C07C 271/44; C07C 271/56
[52] U.S. Cl. ........................................ 560/24; 560/25; 560/26; 560/115; 560/132; 560/157; 560/158; 560/162; 560/163; 560/164
[58] Field of Search ............... 560/24, 25, 26, 115, 560/132, 157, 158, 162, 163, 164

[56] References Cited

U.S. PATENT DOCUMENTS 3,213,155 10/1965 Schriesheim et al. ........... 562/544 X

OTHER PUBLICATIONS

CRC Handbook of Chemistry and Physics, 67th Edition (Boca Raton, Fla.: CRC Press, Inc., 1986–1987) at pp. D-159 to D-160.
E. S. Gould, Mechanism and Structure in Organic Chemistry (Holt, Rinehart and Winston, 1959) at pp. 206, 221, and 229–230.
C. H. DuPuy and K. L. Rinehart, Jr., Introduction to Organic Chemistry (John Wiley & Sons, Inc., 1967) at p. 143.
C. D. Gutsche, The Chemistry of Carbonyl Compounds (Prentice-Hall, Inc., 1967) at pp. 17–19.
S. Julia A. Ginebreda, "Anales de Quimica" Madrid, vol. 75, p. 348, lines 7–13.

*Primary Examiner*—Vivian Garner
*Attorney, Agent, or Firm*—Joseph C. Gil; Richard E. L. Henderson

[57] ABSTRACT

N,N-disubstituted monourethanes and oligourethanes are produced by reacting (a) N-aliphatically and/or N-cycloaliphatically and/or N-araliphatically substituted monourethanes and/or oligourethanes with an alkylating agent in the presence of a solid alkali metal hydroxide. No solvent need by employed but if a solvent is used, that solvent should be an aprotic organic solvent. The alkali metal hydroxide must be used in an equivalent amount. A phase transfer catalyst may optionally be employed. The N,N-disubstituted urethanes obtained by this process are useful in the production of dyes, pharmaceutical products and thermostable synthetic materials.

10 Claims, No Drawings

PROCESS FOR THE PREPARATION OF N,N-DISUBSTITUTED MONO- AND OLIGOURETHANES

BACKGROUND OF THE INVENTION

This invention relates to a process for the preparation of N,N-disubstituted mono and oligourethanes.

It is known that monourethanes can be reacted with lower alkyl halides and alkyl sulphates to form N,N-disubstituted monourethanes (See U. Petersen in Houben-Weyl, Volume E 4, published by Hagemann). However, the known processes have the disadvantage that good results can be obtained only if special, relatively expensive bases such as metal hydrides (e.g., NaH) are used. Furthermore, since the side reaction of olefin formation predominates under these reaction conditions when secondary alkylating agents are used, these processes are restricted to primary alkylating agents.

It is also known that N-aryl substituted monourethanes may be N-alkylated under the conditions of phase transfer catalysis. Although secondary alkylating agents may be used in this process, the method completely fails with N-aliphatically substituted urethanes (See S. Julia, A. Ginebreda, Anales de Quimica (Madrid), Volume 75, page 348, lines 7 to 13). In the examples described in the Anales de Quimica publication, the solvent used is either methylene chloride or dimethyl sulphoxide or methyl ethyl ketone. Triethyl benzyl ammonium chloride is used in all cases as a phase transfer catalyst. These solvents have disadvantages which in some cases considerably reduce the reaction yields. For example, methylene chloride itself acts as an alkylating agent under these reaction conditions while methyl ethyl ketone forms aldol type by-products by auto condensation. Dimethyl sulphoxide forms toxic, malodourous by-products and is difficult to remove from the reaction products.

Furthermore, in many cases the phase transfer catalysts required for the reactions make it difficult to work up the reaction mixtures due to the formation of emulsions. A great effort is required to remove them completely from the reaction products.

SUMMARY OF THE INVENTION

It is an object of the present invention to provide an economical process for alkylating N-mono substituted urethanes which would avoid the disadvantages described above. It has now surprisingly been found that the desired N,N-disubstituted mono and oligourethanes are obtained when N-aliphatically, N-cycloaliphatically or N-araliphatically substituted mono and oligourethanes are reacted with alkylating agents in the presence of an at least equivalent quantity of a solid metal hydroxide, either without solvents or in an aprotic organic solvent. A phase transfer catalyst may optionally be present.

DETAILED DESCRIPTION OF THE INVENTION

The present invention relates to a process for alkylating N-aliphatically monosubstituted urethanes. In this process, N,N-disubstituted mono- and oligourethanes corresponding to the general formula(e)

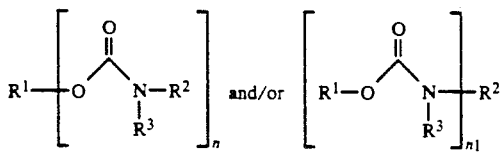

in which
n is an integer from 1 to 6, preferably from 1 to 4,
$n_1$ is an integer from 1 to 6, preferably from 1 to 3,
$R^1$ represents an aromatic hydrocarbon group having 6 to 18 (preferably 6 to 13) carbon atoms, an aliphatic hydrocarbon group having 1 to 18 (preferably 1 to 6) carbon atoms, a cycloaliphatic hydrocarbon group having 4 to 30 (preferably 6 to 15) carbon atoms or an araliphatic hydrocarbon group having 7 to 30 (preferably 7 to 15) carbon atoms,
$R^2$ represents an aliphatic hydrocarbon group having 1-18 (preferably 2-8) carbon atoms, a cycloaliphatic hydrocarbon group having 4-30 (preferably 6-15) carbon atoms or an araliphatic hydrocarbon group having 7-20 (preferably 7-13) carbon atoms,
$R^3$ represents an aromatic hydrocarbon group having 6-18 (preferably 6-13) carbon atoms, an aliphatic hydrocarbon group having 1-18 (preferably 1-12) carbon atoms, a cycloaliphatic hydrocarbon group having 7-30 (preferably 7-15) carbon atoms or an araliphatic hydrocarbon group having 7-30 (preferably 7-15) carbon atoms,
are prepared in high yields by reacting urethanes corresponding to the formula(e)

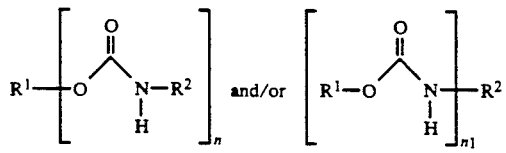

in which n, $n_1$
$R^1$ and $R^2$ have the meanings indicated above with alkylating agents in the presence of at least equivalent quantities of a solid metal hydroxide, either solvent free or in an aprotic organic solvent and optionally in the presence of a phase transfer catalyst.

To obtain high yields, it is particularly advantageous to dissolve the urethane used as starting material, the alkylating agent and any phase transfer catalyst, in an aprotic organic solvent (preferably chlorobenzene, dimethylformamide or N-methyl pyrrolidone) or in an excess of alkylating agent, and then to add the metal hydroxide (preferably sodium or potassium hydroxide) in a solid form, either portionwise or continuously, at low reaction temperatures (e.g., 20° to 30° C.) optionally with cooling, and then to stir, optionally with heating to 50°-80° C., until the reaction has been completed.

If polar aprotic solvents such as dimethylformamide, N-methyl pyrrolidone or dimethyl sulphoxide are used, the addition of a phase transfer catalyst may be omitted without incurring any disadvantages and working up of the reaction mixture is thereby considerably simplified.

Compared with the known processes, the process of the present invention surprisingly provides N,N-di-substituted urethanes by a simpler and more economical procedure and with higher yields, higher volume/time yields and greater purity, especially on a technical scale.

In contrast to the expensive and dangerous metal hydrides used in the known processes, the metal hydroxides used in the present process are less expensive, quite safe and easier to handle.

It must be considered particularly surprising that in contrast to what is stated in the literature, N-aliphatically substituted urethanes can also be alkylated by the process of the present invention.

The urethane used as starting material for the process of the present invention may be prepared, for example, by the reaction of aliphatic mono- or oligoisocyanates with mono- or di- to hexahydric alcohols by known methods, either solvent free or in solution, optionally in the presence of a catalyst.

These urethanes may also be prepared, for example, by the condensation of primary mono- or oligo-amines with chloroformic acid esters of mono- or di- to hexahydric alcohols. They may, of course, also be prepared by the reaction of carbamic acid chlorides with alcohols.

Alcohols which may be used for the preparation of the urethanes used as starting materials in the process of the present invention include alcohols of the formula $$R^1(OH)_n$$

in which n represents an integer from 1 to 6 (preferably 1 to 4), and $R^1$ represents an aromatic hydrocarbon group having 6 to 18 (preferably 6 to 13) carbon atoms, an aliphatic hydrocarbon group having 1 to 18 (preferably 1 to 6) carbon atoms, a cycloaliphatic hydrocarbon group having 4 to 30 (preferably 6 to 15) carbon atoms or an araliphatic hydrocarbon group having 7 to 30 (preferably 7 to 15) carbon atoms.

Such alcohols include monohydric alcohols of the kind described in Ullmanns Enzyklopadie der Technischen Chemie, Volume 7, pages 205–206, 4th Edition, 1974, as well as phenols and substituted phenols.

Examples of suitable polyhydric alcohols are: ethylene glycol, (1,2)- and (1,3)-propylene glycol, (1,4)- and (2,3)-butylene glycol, (1,6)-hexane diol, (1,8)-octanediol, neopentyl glycol, 1,4-bis-hydroxy methyl cyclohexane, 2-methyl-1,3-propanediol, glycerol, trimethylol propane, (1,2,6)-hexanetriol, (1,2,4)-butanetriol, trimethylol ethane, pentaerythritol, quinitol, mannitol, sorbitol, formitol, methylglycoside and/or 1,4-, 3,6-dianhydrohexitols as well as polyvalent phenols such as pyrocatechol, resorcinol, hydroquinone and polynuclear phenols, such as bisphenol A. Mixtures of these alcohols may, of course, also be used.

Isocyanates which may be used for the preparation of the urethanes used as starting materials correspond to the general formula $$R^2(NCO)_{n_1}$$

in which $n_1$ represents an integer from 1–6 (preferably 1–3), and $R^2$ represents an aliphatic hydrocarbon group having 1–18 (preferably 2–8) carbon atoms, a cycloaliphatic hydrocarbon group having 4–30 (preferably 6–15) carbon atoms or an araliphatic hydrocarbon group having 7–20 (preferably 7–13) carbon atoms.

Specific examples of such isocyanates include: isocyanato-methane, -ethane, -propane, -butane, -pentane, and -hexane; 6-chlorohexyl isocyanate; isocyanatocyclohexane; benzyl isocyanate; tetramethylene diisocyanate; hexamethylene diisocyanate; decamethylene diisocyanate; 1,3-di-(3-isocyanatopropoxy)-2,2-dimethyl propane; (1,4)-cyclohexane diisocyanate, (2,4)-methyl cyclohexane diisocyanate, methyl cyclohexane (2,6)-diisocyanate; 1,3-diisocyanatocyclohexane; mixtures of (2,4)-methyl cyclohexane diisocyanate and (2,6)-methyl cyclohexane diisocyanate; dicyclohexyl methane-4,4'-diisocyanate; 1-isocyanato-3-isocyanato-methyl-3,5,5-trimethyl-cyclohexane (isophorone diisocyanate); 1,2-di-(iso- cyanato-methyl)-cyclobutane; m- and p-xylylene diisocyanate; $\alpha,\alpha,\alpha',\alpha'$-tetramethyl-m- and/or p-xylylene diisocyanate and hexahydroxylylene diisocyanate. In the case of cycloaliphatic diisocyanates, any stereoisomers or mixtures of these compounds may be used.

Mixtures of the above-mentioned isocyanates may, of course, also be used.

The alkylating agents used in the process of the present invention include those corresponding to the formula $$R^3X$$

in which $R^3$ represents an aromatic hydrocarbon group having 6–18 (preferably 6–13) carbon atoms, an aliphatic hydrocarbon group having 1–18 (preferably 1–12) carbon atoms, a cycloaliphatic hydrocarbon group having 7–30 (preferably 7–15) carbon atoms or an araliphatic hydrocarbon group having 7–30 (preferably 7–15) carbon atoms, and X represents a suitable removable substituent such as halogen atom or a sulfate, sulfonate, phosphate or phosphonate group.

The hydrocarbon $R^3$ may, of course, carry other functional groups in addition to the group X, provided they are inert under the reaction conditions or react in a well defined manner with the reactants according to the invention. Examples of such functional groups include: nitro groups, certain ester, urethane, amide and sulfonyl groups, unactivated, aromatically bound halogen, epoxide groups, aziridine groups, ether groups and thioether groups.

Specific examples of suitable alkylating agents include: methylchloride and bromide, ethylchloride and bromide, propylchloride and bromide, i-propylchloride and bromide, n-butylchloride and bromide, isobutylchloride and bromide, cyclohexylchloride and bromide, octyl, nonyl, decyl, undecyl and dodecyl chloride and bromide, benzyl chloride and bromide, allylchloride and bromide, p-nitro benzylchloride and bromide, 2,4-dinitrochlorobenzene, 2,4-dinitrofluorobenzene, 2,4,6-dinitrochlorobenzene, 2,4,6-dinitrofluorobenzene, dimethylsulfate, diethyl sulfate, the methyl ester and ethyl ester of p-toluene sulfonic acid, ethylene chlorohydrin, ethylene bromo- hydrin and epichlorohydrin.

Mixtures of these alkylating agents may, of course, also be used.

The following are particularly preferred alkylating agents: methyl chloride and bromide, ethyl chloride and bromide, dodecyl chloride and bromide, allylchloride and bromide, benzyl chloride and p-tosyl ester.

When readily volatile alkylating agents such as methylene chloride or bromide or ethyl chloride are used, the reaction is preferably carried out in an autoclave under pressure.

The reaction of urethane with alkylating agent may be carried out either in an aprotic organic solvent or in excess, liquified alkylating agent, optionally in the presence of a phase transfer catalyst.

The bases used in the process of the present invention are solid, preferably finely powdered metal hydroxides such as alkali metal hydroxides (e.g., potassium or sodium hydroxide). Sodium hydroxide is preferred on economic grounds. The hydroxide of lithium, rubidium or barium, for example, or moist silver oxide may, of course, also be used. It may in some cases be advantageous to use mixtures of these metal hydroxides.

The metal hydroxides are used in equivalent quantities based on the amount of urethane groups. The above described urethanes used as starting materials may be reacted with the alkylating agent in stoichiometric quantities, less than stoichiometric quantities or in excess (based on the number of urethane groups present in the molecule). It is preferred to use 0.3-5 mol, particularly 1-2 mol of alkylating agent for each mol of urethane groups. Only partial alkylation is, of course, obtained when a subequivalent quantity of alkylating agent is used but the use of a substantial excess of alkylating agent is uneconomical.

The process of the present invention is generally carried out at a temperature of 0°-180° C., preferably 10°-80° C. and most preferably at room temperature, under excess pressure or reduced pressure or, preferably without application of pressure, and either continuously or batch-wise.

The dwell time may be, for example, 0.5 to 24 hours and is preferably in the region of 0.5 to 10 hours.

The reaction may be carried out in excess alkylating agent, or preferably, in an aprotic organic solvent.

Aprotic organic solvents which are inert under the reaction conditions according to the invention may be used. Examples of such solvents are those described in Ullmanns Enzyklopadie der Technischen Chemie Volume 14, 4th Edition, Verlag Chemie 1978, page 305. Specific examples of suitable solvents include: benzene, toluene, xylene, ethylbenzyl, cumene, methylene chloride, chloroform, dichlorobenzene, trichlorobenzene, nitrobenzene, acetone, methylethyl ketone, diethyl ketone, cyclohexanone, diethyl ether, diisopropyl ether, tetrahydrofuran, dioxane, dimethylformamide, dimethyl acetamide, dimethyl sulfoxide, tetramethylene sulfone, furfurol. nitromethane, nitroethane, nitropropane, N-methyl pyrrolidone and hexamethylene phosphonic acid triamide. Chlorobenzene, dimethylformamide, N-methyl pyrrolidone and tetramethylene sulfone are preferred.

Mixtures of these solvents may, of course, also be used.

It may in some cases be advantageous to carry out the reaction in the presence of a phase transfer catalyst. Catalysts of this kind are described, for example, by E. V. and S. S. Dehmlow in Phase Transfer Catalysis, 2nd Edition, Verlag Chemie 1983. Quaternary ammonium and phosphonium salts corresponding to the formula:

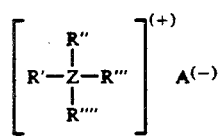

are suitable catalysts. In the above formula,

Z represents nitrogen or phosphorus and R', R'',R''' and R'''', which may be identical or different, each represents an alkyl group with 1-18 carbon atoms although one of the groups may be an araliphatic group containing 7-15 carbon atoms, and the sum of carbon atoms of the four groups is preferably 12 to 29 and $A^{(-)}$ represents an halogenide or phosphonate.

The following are typical examples of suitable catalysts: N-benzyl-N,N,N-triethyl-ammonium chloride or bromide, N-benzyl-N-dodecyl-N,N-dimethyl-ammonium chloride or bromide, N,N,N,N-tetra-n-hexyl-ammonium chloride or bromide, N-benzyl-N,N,N-tri-n-octyl-ammonium chloride or bromide and phosphonium salts corresponding to these ammonium salts.

The quaternary ammonium and phosphonium salts mentioned as examples are preferably put into the process of the present invention in a solvent free form or as aqueous solutions (for example, with a solids content of 30 to 60 wt. %) and preferably in a quantity of 1-10 mol %, based on the molar number of urethane groups present.

Phase transfer catalysts may be omitted without any deleterious effect if polar aprotic solvents such as dimethylformamide, N-methyl-pyrrolidone, dimethyl sulfoxide or sulfolan are used.

The process according to the invention may be carried out, for example, by introducing the urethane, alkylating agent and optional catalyst into the selected solvent and the solid, finely ground metal hydroxide may then be added either portion-wise or continuously with stirring and optionally cooling. The reaction mixture may then be stirred at room temperature or optionally at elevated temperature until thin layer chromotographic or gas chromatographic analysis shows complete conversion.

The product may be worked up by known methods. When water-miscible solvents are used and the reaction products are solid and insoluble in water, the reaction mixture may be stirred into water and the precipitated reaction product may then be isolated by suction filtration in the usual manner. If the reaction products are oily, they are suitably worked up by one of the usual methods of extraction. The crude products may, if necessary, be purified by conventional methods such as recrystallization or distillation.

The N,N-disubstituted urethanes which may be prepared by the process of the present invention are active ingredients and valuable starting materials for the preparation of dyes, pharmaceutical products and thermostable synthetic materials. The N,N-disubstituted urethanes produced in accordance with the present invention in particular show greater thermal, thermooxidative and photooxidative stability (see R. Vieweg, A. Hochtlen, Kunststoff Handbuch Volume VII, Polyurethane, Hanser Verlag, Munich 1966, pages 11 and 21) and better fire characteristics than the corresponding N-monosubstituted urethanes.

The corresponding substituted secondary amines may be prepared by hydrolysis of the N,N-disubstituted urethanes. These amines are also important starting materials for the synthesis of active ingredients and the preparation of formulations for synthetic materials.

The invention is further illustrated but is not intended to be limited by the following examples in which all parts and percentages are by weight unless otherwise specified.

EXAMPLES

All the reaction products were tested for purity by gas chromatography or thin layer chromatography and their identity was confirmed by IR and NMR Spectra.

IR spectroscopy in particular provides a convenient method of checking the rate of conversion since the characteristic bands for N-monosubstituted urethanes at 3200–3500 cm$^{-1}$ (N—H) and 1530–1560 cm$^{-1}$ (N—H) disappear in the course of the reaction.

EXAMPLE 1

16 g of powdered sodium hydroxide were added portion-wise in the course of 2 hours to a solution of 58.1 g of N-6-chlorohexyl-carbamic acid methyl ester and 51.7 g of diethyl sulfate in 300 ml of dimethyl-formamide (DMF) with stirring at 20° C. When all the sodium hydroxide had been added, stirring was continued for a further 3 hours at room temperature and the solvent was then evaporated off under vacuum and the residue was taken up in 700 ml of methylene chloride. The organic phase was washed, first with saturated NH$_4$Cl solution and then with water, and dehydrated over Na$_2$SO$_4$. After evaporation of the solvent, the oily crude product was fractionated in a high vacuum.

Yield: 47.8 g (72%), b.p.: 90° C./0.13 mbar. (colorless oil).

EXAMPLE 2

52.4 g of N-tertiary butyl-carbamic acid methyl ester, 57 g of benzyl chloride and 18 g of powdered sodium hydroxide were reacted in 300 ml of DMF in the same manner as in Example 1.

After-stirring time: 15 hours (h) at 50° C.

Yield: 43.3 (49%), b.p.: 90° C./0.13 mbar (colorless oil).

EXAMPLE 3

49.5 g of N-benzyl-carbamic acid methyl ester, 25.2 of allyl chloride and 13.2 g of powdered sodium hydroxide were reacted in 300 ml of DMF in the same manner as in Example 1.

After-stirring time: 15 h at 25° C.

Yield: 51.1 g (83%), b.p.: 118° C./0.16 mbar (colorless oil).

EXAMPLE 4

49.5 of N-benzyl-carbamic acid methyl ester, 48 g of n-butyl bromide and 14 g of powdered sodium hydroxide were reacted in 300 ml of DMF in the same manner as in Example 1.

After-stirring time: 15 h at 50° C.

Yield: 50.4 g (76%), b.p.: 110° C./0.2 mbar (colorless oil).

EXAMPLE 5

49.5 g of N-benzyl-carbamic acid methyl ester, 48 g of n-butyl bromide, 12.1 g of methyl-tridecyl-ammonium chloride and 14 g of powdered sodium hydroxide were reacted in 400 ml of chlorobenzene in the same manner as in Example 1.

After-stirring time: 15 h at 50° C.

Yield: 45.1 g (68%), b.p.: 110° C./0.2 mbar (colorless oil).

EXAMPLE 6

49.5 g of N-benzyl-carbamic acid methyl ester, 61.4 g of p-toluene sulphonic acid methyl ester and 13.2 g of powdered sodium hydroxide were reacted in 300 ml of DMF in the same manner as in Example 1.

After-stirring time: 15 h at 25° C.

Yield: 48.9 g (92%), b.p.: 96° C./0.44 mbar (colorless oil).

EXAMPLE 7

49.5 g of N-benzyl-carbamic acid methyl ester, 49.2 g of 2-bromopropane and 16 g of powdered sodium hydroxide were reacted in 400 ml of DMF by the method described in Example 1.

After-stirring time: 15 h at 25° C.

Yield: 19.9 g (32%), b.p.: 89° C./0.45 mbar (colorless oil).

EXAMPLE 8

49.5 g of N-benzyl-carbamic acid methyl ester, 67.5 g of dodecyl chloride and 24 g of powdered sodium hydroxide were reacted in 400 ml of DMF by the method described in Example 1.

After-stirring time: 15 h at 50° C.

Yield: 85 g (85%) (yellowish oil).

EXAMPLE 9

49.5 g of N-benzyl-carbamic acid methyl ester, 30.5 g of epichlorohydrin, 9.7 g of tetrabutyl ammonium bromide and 18.5 g of powdered potassium hydroxide were reacted in 400 ml of chlorobenzene by the method described in Example 1.

After-stirring time: 15 h at 25° C.

Yield: 37.8 g (57%), b.p.: 135° C./0.53 mbar (colorless oil).

EXAMPLE 10

46.4 g of diurethane (prepared from hexamethylene diisocyanate and methanol), 81.8 g of p-toluene sulfonic acid methyl ester and 17.6 g of powdered sodium hydroxide were reacted in 400 ml of N-methyl-pyrrolidone (NMP) by the method described in Example 1.

After-stirring time: 15 h at 50° C.

Yield: 42.6 g (82%) (colorless oil).

EXAMPLE 11

46.4 g of diurethane (prepared from hexamethylene diisocyanate and methanol), 942 g of allyl chloride and 22 g of powdered sodium hydroxide were reacted in 300 ml of DMF in the same manner as in Example 1.

After-stirring time: 15 h at 50° C.

Yield: 55.5 g (89%), b.p.: 159° C./0.11 mbar (colorless oil).

EXAMPLE 12

57.2 g of diurethanes (prepared from isophorone diisocyanate and methanol), 9,101.3 g of benzyl chloride and 32 g of powdered sodium hydroxide were reacted in 500 ml of tetramethylene sulfone (Sulfolan ®) by the method described in Example 1.

After-stirring time: 15 h at 60° C.

Yield: 71 g (76%) (yellowish oil).

EXAMPLE 13

57.5 g of diurethane (prepared from 1,4-cyclohexane diisocyanate and methanol), 42.1 g of allyl chloride and 22 g of powdered sodium hydroxide were reacted in 500 ml of N-methyl-pyrrolidone by the method described in Example 1.

After-stirring time: 15 h at 50° C.

Yield: 60.5 g (78%) (yellowish oil).

EXAMPLE 14

65.6 g of diurethane (prepared from benzyl isocyanate and ethylene glycol), 63.3 g of benzyl chloride and 20 g of powdered sodium hydroxide were reacted in 500 ml of DMF by the method described in Example 1.

After-stirring time: 15 h at 50° C.

Yield: 95.5 g (94%), m.p.: 102° C. (colorless crystals of isopropanol).

EXAMPLE 15

53.3 g of triurethane (prepared from benzyl isocyanate and trimethylol propane), 25.3 g of allyl chloride and 18.5 g of powdered potassium hydroxide were reacted in 300 ml of tetramethylene sulfone by the method described in Example 1.

After-stirring time: 15 h at 50° C.

Yield: 50.9 g (78%) (yellowish oil).

EXAMPLE 16

49.5 g of N-benzyl-carbamic acid methyl ester, 66.8 g of 2,4-dinitrochlorobenzene and 13.2 g of powdered sodium hydroxide were reacted in 400 ml of DMF by the method described in Example 1.

After-stirring time: 15 h at 50° C.

Yield: 37.8 g (38%) (violet resin)

EXAMPLE 17

49.5 g of N-benzyl-carbamic acid methyl ester, 12.8 g of powdered sodium hydroxide and 6.8 g of triethyl benzyl ammonium chloride were reacted in 200 ml of benzyl chloride by the method described in Example 1.

After-stirring time: 3 h at 50° C.

Yield: 64.3 g (84%), b.p.: 139° C./0.16 mbar (colorless oil).

EXAMPLE 18

33 g of N-benzyl-carbamic acid methyl ester, 8.8 g of powdered sodium hydroxide and 4.5 g of triethyl benzyl ammonium chloride were reacted in 100 ml of n-butyl bromide by the method described in Example 1.

After-stirring time: 3 h at 80° C.

Yield: 26.1 g (59%), b.p.: 110° C./0.2 mbar (colorless oil).

EXAMPLE 19

82.5 g of N-benzyl-carbamic acid methyl ester, 70 g of benzyl chloride, 21 g of powdered sodium hydroxide and 11.3 g of triethyl benzyl ammonium chloride were reacted solvent free by the method described in Example 1.

Yield: 68.9 g (54%), b.p.: 139° C./0.16 mbar. (colorless oil).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of N,N-disubstituted monourethanes and oligourethanes in which
   (a) an N-aliphatically and/or N-cycloaliphatically and/or N-araliphatically monosubstituted monourethane and/or oligourethane is reacted with
   (b) an alkylating agent
   in the presence of
   (c) an equivalent amount of a solid metal hydroxide in the absence of a solvent or in the presence of an aprotic organic solvent.

2. The process of claim 1 in which the reaction is carried out in the presence of (d) a phase transfer catalyst.

3. The process of claim 1 which is carried out in the absence of a solvent.

4. The process of claim 3 in which alkylating agent (b) is used in excess.

5. The process of claim 1 in which the reaction is carried out in the presence of an apolar, aprotic organic solvent.

6. The process of claim 5 in which the reaction is carried out in the presence of (d) a phase transfer catalyst.

7. The process of claim 1 which is carried out in the presence of chlorobenzene, dimethyl formamide, N-methyl pyrrolidone or tetramethylene sulfone.

8. The process as claimed in claim 1, in which as monosubstituted monourethane and/or oligourethane urethanes corresponding to the formula(e)

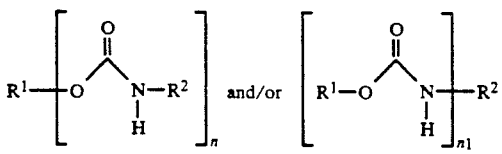

in which n and $n_1$ is an integer from 1 to 6, $R^1$ represents an aromatic hydrocarbon group having 6 to 18 carbon atoms, an aliphatic hydrocarbon group having 1 to 18 carbon atoms, a cycloaliphatic hydrocarbon group having 4 to 30 carbon atoms or an araliphatic group having 7 to 30 carbon atoms are used $R^2$ represents an aliphatic hydrocarbon group having 1-18 carbon atoms, a cycloaliphatic hydrocarbon group having 4-30 carbon atoms or an araliphatic hydrocarbon group having 7-20 carbon atoms are used.

9. The process as claimed in claim 1, wherein as alkylating agent a compound of the general formula $R^3X$, wherein $R^3$ represents an aromatic hydrocarbon group having 6-18 carbon atoms, an aliphatic hydrocarbon group having 1-18 carbon atoms, a cycloaliphatic hydrocarbon group having 7-30 carbon atoms or an araliphatic hydrocarbon group having 7-30 carbon atoms, and X represents a halogen atom or a sulfate, sulfonate, phosphate or phosphonate group, is used.

10. The process as claimed in claim 9, wherein as alkylating agent a member of the group consisting of methyl chloride and bromide, ethyl chloride and bromide, dodecyl chloride and bromide, allylchloride and bromide, benzyl chloride and p-tosyl ester is used.